United States Patent [19]
Langer et al.

[11] Patent Number: 5,459,126
[45] Date of Patent: Oct. 17, 1995

[54] METHOD FOR DECREASING CALCIUM UPTAKE BY CELLS USING SELECTED POLYCATIONS

[75] Inventors: Glenn A. Langer, Pacific Palisades, Calif.; Jonathan R. Clague, London, England; Jan A. Post, Nieuwegein, Netherlands

[73] Assignee: California Institute of Technology, Pasadena, Calif.

[21] Appl. No.: 65,631

[22] Filed: May 21, 1993

[51] Int. Cl.⁶ .......................... A61K 37/00; A61K 31/14; A61K 31/02
[52] U.S. Cl. .................. 514/2; 514/11; 514/642; 514/743; 514/12; 514/21
[58] Field of Search ...................... 514/2, 11, 12, 514/21, 642, 743

[56] References Cited

U.S. PATENT DOCUMENTS 4,692,433 9/1987 Hostettler et al. .................. 514/12
4,719,201 1/1988 Foker .................................... 514/23

OTHER PUBLICATIONS

Claque, et al., "Cationic Amphiphiles Prevent Calcium Leak Induced by ATP Depletion in Myocardial Cells", Jan. 1993, pp. 214–218.

Burton; Superoxide dismutase enhances recovery following mycardial ischemic, Am. J. of Physiol.; 248:H637–H643 (1985).

Primary Examiner—Theodore J. Criares
Attorney, Agent, or Firm—Poms, Smith, Lande & Rose

[57] ABSTRACT

A method for reducing calcium overload in cells to prevent the transition from reversible to irreversible injury. The cell surface is treated with an organic polycation selected from the group consisting of protamine, dodecyltrimethylammonium bromide, polymyxin B sulfate and polybrene which is capable of altering the cells surface charge sufficiently to eliminate or reduce the influx of calcium resulting from exposure to noxious stimuli. The method may be used both in vivo and in vitro. The method is effective in preventing calcium uptake in a variety of cell injury situations including metabolic inhibition and free radical attack.

17 Claims, 5 Drawing Sheets

METHOD FOR DECREASING CALCIUM UPTAKE BY CELLS USING SELECTED POLYCATIONS

BACKGROUND OF THE INVENTION

This invention was made with support under Grant Number 5R01 HL28539-10 from the National Institutes of Health. Accordingly, the U.S. Government has certain rights in the invention.

1. Field of the Invention

The present invention relates generally to intracellular calcium overload, also known as calcium leak, which plays a role in the transition from reversible to irreversible injury during ischemia/reperfusion in cells. More particularly, the present invention relates to methods for reducing the uptake of calcium during such overload or leak conditions to reduce or prevent cell death.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

It is well-known that excessive calcium influx represents the final common pathway in cell death(1). An increase in intracellular calcium has been demonstrated in response to a variety of noxious stimuli including ischemia(2), hypoxia-reoxygenation(3), metabolic inhibition(4) and reperfusion(2,5). Elevated levels of intracellular calcium are thought to be of importance in the transition from reversible to irreversible injury in cardiac(5) and other cell types(6).

Although the pathogenesis of the calcium leak has been the subject of considerable research, the exact mechanism remains to be established. One proposed mechanism is the Na-Ca exchanger operating in reversed mode secondary to a rise of intracellular sodium which has been documented early in ischemia(7,8). Further support for this proposed mechanism has been provided by the demonstration that the oxygen radical scavenger 1,3-dimethyl-2-thiourea(DMTU) protects rat ventricular myocytes against hypoxia(9). DMTU was shown to be an inhibitor of Na-Ca exchange. Accordingly, it was concluded that Ca influx in hypoxia occurs via Na-Ca exchange.

Other calcium leak mechanisms have been proposed in addition to the above suggested reversal of Na-Ca exchanger activity. These other mechanisms include: calcium leak through defects in the sarcolemma(SL); calcium leak via the voltage-activated calcium channels; or calcium leak through specific calcium leak channels which have been recently identified in cardiac and other cells(10,11,12).

There presently is a need to provide further elucidation of the mechanisms by which calcium leak occurs and the role played by elevated calcium levels in cell death. Equally important is the need to provide methods which are capable of controlling calcium leak in order to prevent, or at least reduce, the leakage of calcium into cells during exposure to noxious stimuli. Such methods will be useful in avoiding cell damage or death.

SUMMARY OF THE INVENTION

In accordance with the present invention, a method is provided for reducing the uptake or influx of calcium into a mammalian cell by treating the cell surface with a cationic agent. It was discovered that alteration of the cell surface charge by treatment with a cationic agent provides an effective procedure for eliminating, or at least reducing, the amount of calcium transported into the cell during exposure to a noxious stimuli.

The method may be used to treat cells either in vivo or in vitro. The method requires the exposure of the cell surface to an amount of a cationic agent which alters the cell surface charge a sufficient amount to reduce calcium uptake without disrupting the cell. The method is well-suited for treating muscle cells, such as cardiac myocytes. The method is applicable to cells having a sarcolemma or to cells in general which have calcium leak channels.

As a feature of the present invention, it was discovered that the level of charge on the cationic agent is directly related to the ability of the agent to prevent calcium uptake. Accordingly, strong organic poly-cationic agents, such as protamine and polymyxin B sulfate (PXB) are especially effective in limiting calcium influx.

The method of the present invention is effective in reducing calcium uptake by cells in a variety of noxious situations. These situations include metabolic inhibition and free radical attack. This versatility makes the method useful as part of a general therapeutic approach to prevent or substantially reduce cell death resulting from calcium influx.

The above discussed and many other features and attendant advantages of the present invention will become better understood by reference to the following detailed description when taken in conjunction with the accompanying drawings.

DETAILED DESCRIPTION OF THE PREFERRED EMBODIMENTS

The present invention involves a method for reducing the uptake of calcium by mammalian cells which are under the influence of a noxious stimuli. The type of noxious stimuli which create calcium uptake include, for example, metabolic inhibition, anoxia, ischemia and free radical attack. The following detailed description will be limited to reducing calcium uptake in cells subjected to metabolic inhibition or free radical attack with it being understood by those skilled in the art that the method has wide application to any situation where a cell is undergoing calcium uptake or influx in response to a noxious stimulus.

The method in accordance with the present invention requires that the cell surface be treated with a sufficient amount of a cationic agent to alter the surface charge of the cell to reduce or prevent the uptake of calcium caused by the noxious stimuli. The amount of cationic agent which is used will vary depending upon the particular cationic agent, the particular cell type, the type of noxious stimulus to which the cell is being exposed, and the particular treatment process, ie. in vivo or in vitro treatment. The specific amount can be easily determined experimentally for each different situation. Some general guidelines with respect to amounts of cationic agents will be given below in connection with the description of specific examples.

The mammalian cell types which are amenable to treatment by the present invention include any mammalian cell which undergoes calcium uptake when exposed to noxious stimuli. The invention is especially well-suited for treating cells, such as muscle cells, which have a sarcolemma. Exemplary cells include cardiac myocytes, in which the uptake has been directly demonstrated. Other cells which have been demonstrated to have calcium leak channels would be expected to respond similarly, e.g. dystrophic skeletal muscle(12).

The cationic agents which are suitable include organic cations such as protamine, dodecyltrimethylammonium bromide(DDTMA), polymyxin B sulfate and polybrene. The greater the cationic charge, the more effective the agent. It is preferred that the cation carry as large a positive charge as possible without causing damage to the cell surface or otherwise disrupting the cell environment, especially when treatment is conducted in vivo. Organic cations with relatively small positive charge are not preferred. Gentamicin and other aminoglycoside antibiotics are not preferred because of their relatively low cationic charge. It was found that relatively large amounts (1.5 mM) of these types of cationic agents were required in order to obtain any significant levels of calcium uptake inhibition.

The procedure for exposing the cell surface to the cationic agent can vary widely provided that a sufficient amount of cationic agent is present to alter the cell surface sufficiently to reduce the uptake of calcium. For in vitro situations, the cationic agent is simply added to the cell culture. The concentration of cationic agent in the cell culture preferably will range from 5 μM to 50 μM for strong cationic agents. For example, cell culture concentrations of protamine at levels of 5 μM and above were found to completely prevent calcium overload.

For in vivo situations, the cationic agent is preferably added to a pharmaceutically acceptable solution which is administered to the mammal. The cationic solution is preferably administered intravenously. The concentration of cationic agent in the pharmaceutically acceptable solution is chosen so that the ultimate concentration of cationic agent in the environment immediately surrounding the cell will be at least 5 μM. It is preferred that the minimum amount of cationic agent be utilized which is effective in eliminating calcium uptake so that any adverse effects on other cells in the body are minimized. Suitable pharmaceutically acceptable solutions include saline or glucose solutions. The concentration of cationic agent in the pharmaceutically acceptable solution will range from about 5 μM to about 50 μM.

Examples of practice are as follows:

EXAMPLE 1

The following example demonstrates the use of protamine to prevent the uptake of calcium by neonatal rat cardiomyocytes exposed to hydrogen peroxide.

Protamine is a strong polycationic polypeptide used extensively for heparin reversal after cardiopulmonary bypass. The drug is known to be negatively inotropic. The neonatal rat cardiomyocytes were cultured according to the procedure described by Frank et al.(13).

Ca fluxes were measured by an on-line isotopic technique (13). The myocytes were cultured onto scintillant-containing discs which were mounted in a flow cell so that the cells were in direct contact with perfusate. The flow cell was placed between two opposing spectrophotometer tubes. Cell-associated Ca was then recorded in counts per minute. $^{45}Ca^{2+}$ is a low energy beta-emitter. The radioactivity contained within the perfusate is counted with very low efficiency (<5%) whereas that within the cells is counted with an efficiency of 39%. In all of the examples the cells were initially perfused with non isotopic solution to remove any debris. Perfusion with $^{45}Ca^{2+}$ containing solution was then commenced at 10 ml/minute and continued until the cells were labelled to asymptote. This normally took 25–30 minutes. The flow cell was then drained and refilled with a solution containing hydrogen peroxide. The cells were then incubated for 60 minutes with continuous recording of $^{45}Ca$ labeling (no flow) prior to washout with non-isotopic perfusate.

After asymptotic labeling with $^{45}Ca$, the cells were perfused with a solution containing protamine sulfate at varying concentrations. This did not significantly alter Ca uptake. The flow cell was then drained and refilled with a solution containing 50 μM $H_2O_2$ and protamine. The procedure was repeated with protamine in varying concentrations: 1 μM (n=4); 5 μM (n=6) and 50 μM (n=6).

At the end of each experiment the discs were removed from the flow cell, allowed to dry and the cells were scraped onto a pre-weighed piece of filter paper. This was placed in an oven (>100° C.) overnight and then weighed, permitting determination of the cellular dry weight. The specific activity of each isotopic solution was measured in a spectrophotometer (Beckman Instruments) and cell-associated Ca was expressed in mmoles/kg dry cellular weight. The cell cultures were maintained at 37° C.

Figure 1:
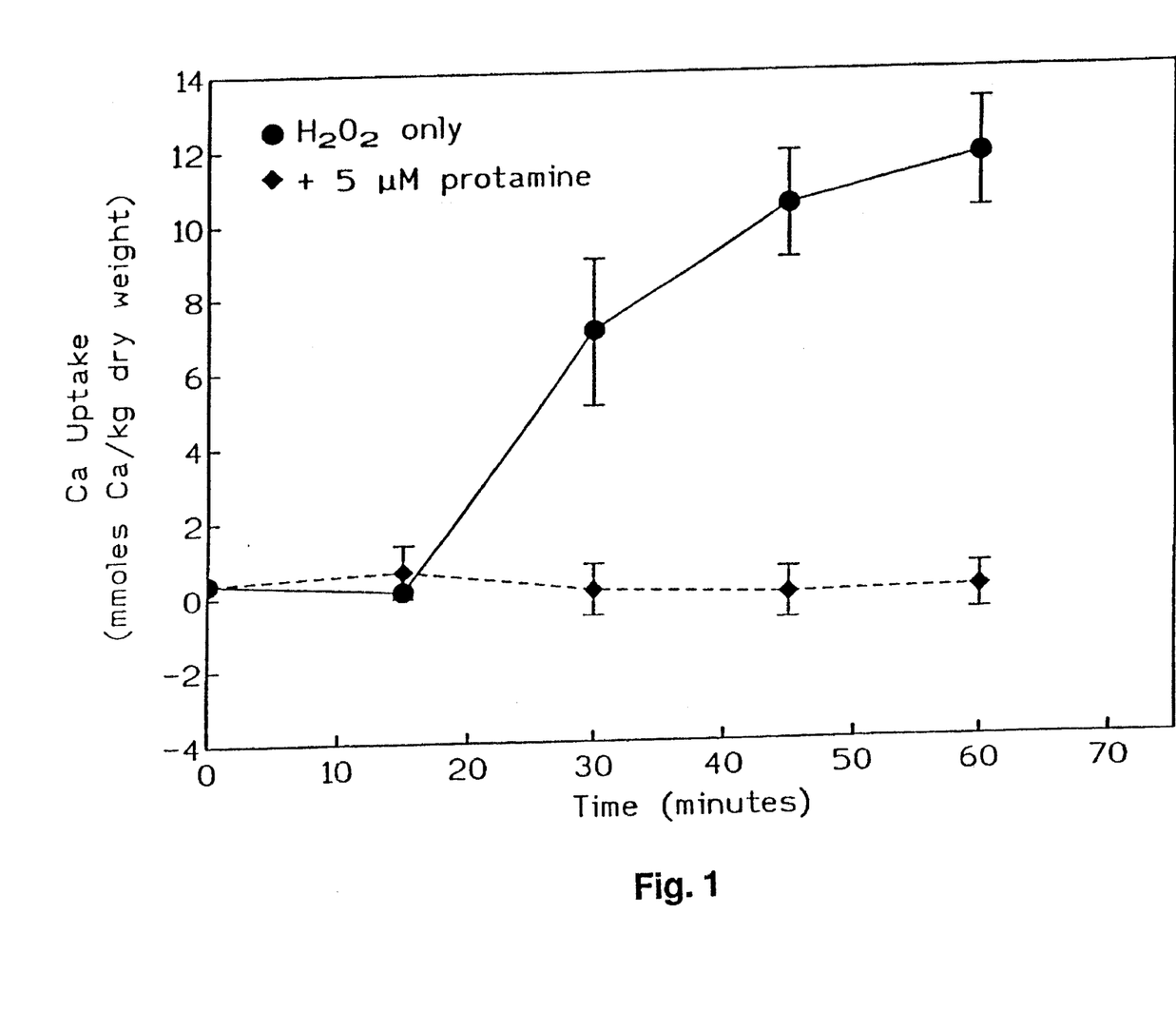
FIG. 1 is a graph of test results showing the prevention of calcium uptake by treatment of cells with protamine where the cells have been subjected to free radical attack and the protamine concentration is 5 µM.
Figure 2:
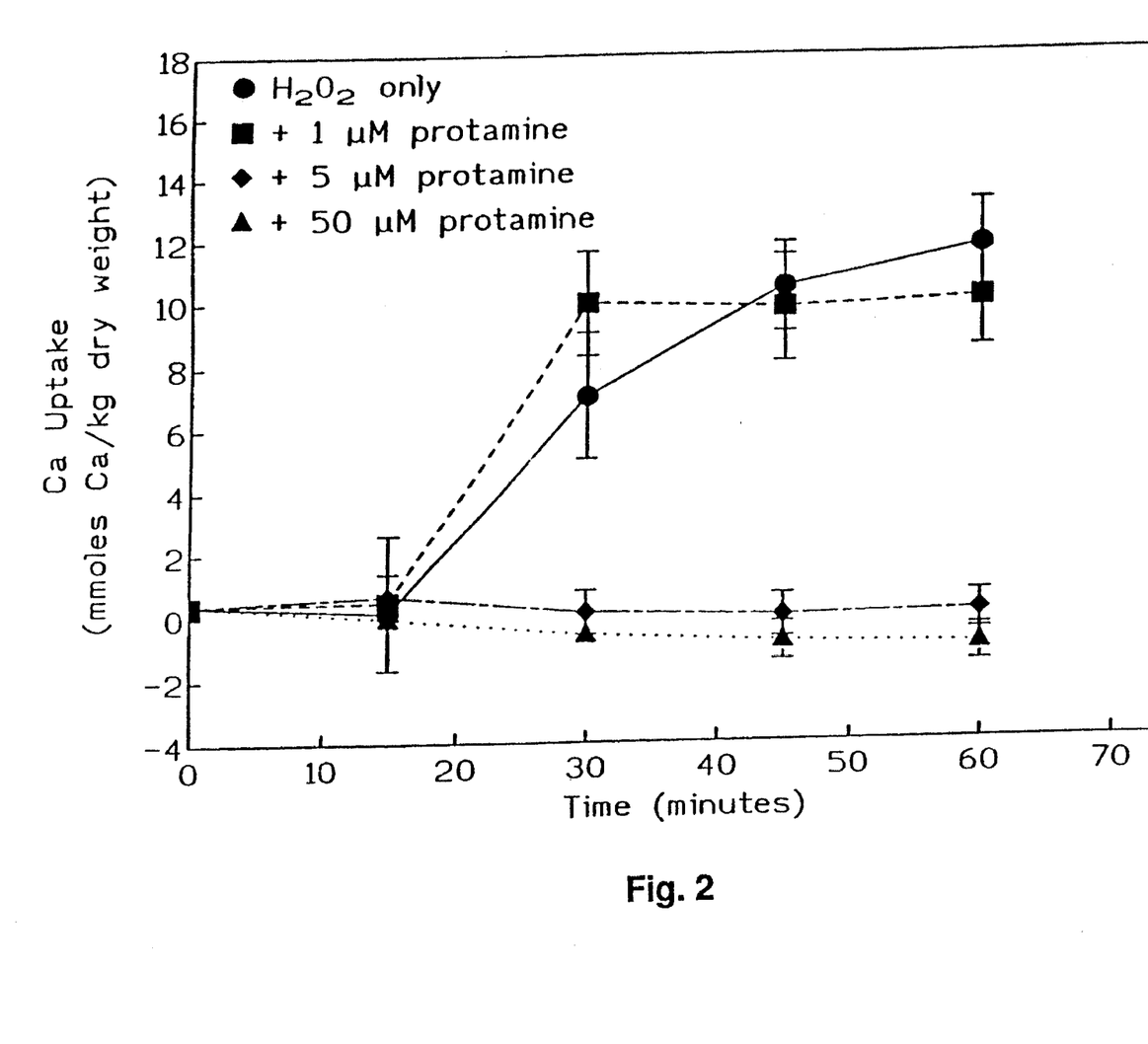
FIG. 2 is a graph of test results showing the effect of treatment in accordance with the present invention using different concentrations of protamine.

At a concentration of 1 μM, protamine had no effect. At 5 μM, protamine completely prevented the Ca overload. Increasing the concentration above 5 μM had no additional effect. The results of the test for a protamine concentration of 5 μM is shown in FIG. 1. FIG. 2 shows the test results for various concentrations of protamine.

The effect of protamine, as described in this example was completely inhibited by neutralizing its positive charge with heparin. It is believed that the agent must have a positive charge which is sufficient to alter surface charge of the outer sarcolemmal leaflet. This penetration is necessary in order for the cation to exert its effect at the cell surface.

EXAMPLE 2

The following example demonstrates the use of protamine to prevent the uptake of calcium by neonatal rat cardiomyocytes which are metabolically inhibited.

Figure 3:
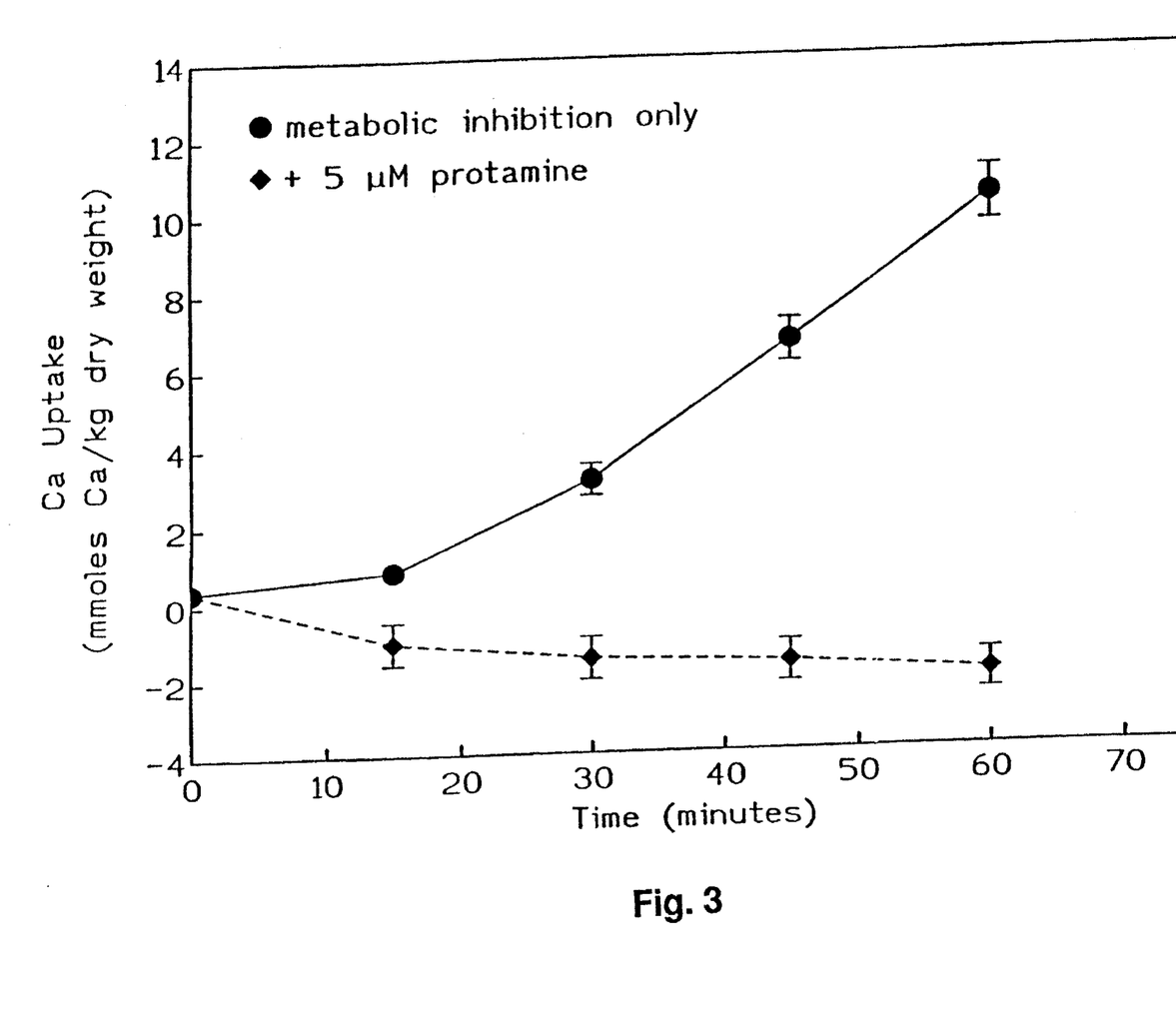
FIG. 3 is a graph of test results showing the prevention of calcium uptake by treatment of cells with protamine where the cells have been metabolically inhibited and the protamine concentration is 5 µM.

Exposure of neonatal rat cardiomycytes to 0.05 mM iodoacetic acid (IAA), as a glycolytic inhibitor, and 0.5 mM 2-deoxyglucose (2-DOG), as a non-metabolizable substrate, produces a graded depletion in intracellular ATP and induces a significant Ca leak. In the following example involving metabolic inhibition, these two compounds were included in the incubation medium. 2-DOG was added directly and IAA was added from a 1 M stock solution, dissolved in water. The concentration in the culture media was 0.5 mM for 2-DOG and 0.05 mM for IAA. The metabolically inhibited cells were treated with protamine in the same manner as Example 1. The results were similar to Example 1, i.e. protamine did not exert a significant effect at concentrations below 5 μM. At concentrations of 5 μM and higher, protamine provided a dramatic drop in calcium uptake. The results of this example are summarized and shown in FIG. 3.

EXAMPLE 3

The following example demonstrates the use of polybrene (hexamedronium bromide) to prevent the uptake of calcium by neonatal rat cardiomyocytes which have been exposed to hydrogen peroxide or are metabolically inhibited. Polybrene is a synthetic polycationic compound which is commercially available. The magnitude of the positive charge borne by the molecule is less than that of protamine.

Figure 4:
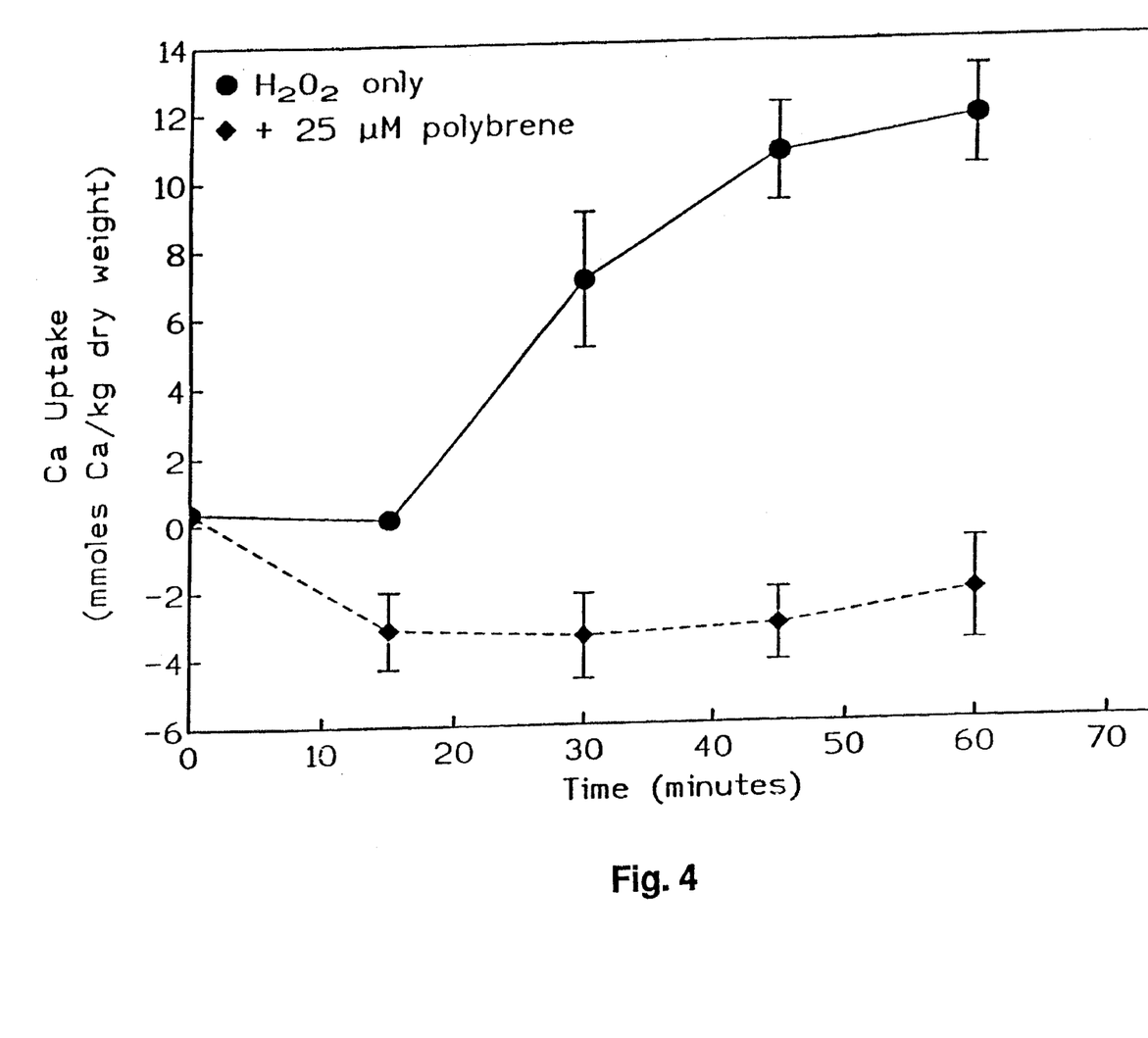
FIG. 4 is a graph of test results showing the prevention of calcium uptake by treatment of cells with polybrene where the cells have been subjected to free radical attack and the polybrene concentration is 25 µM.
Figure 5:
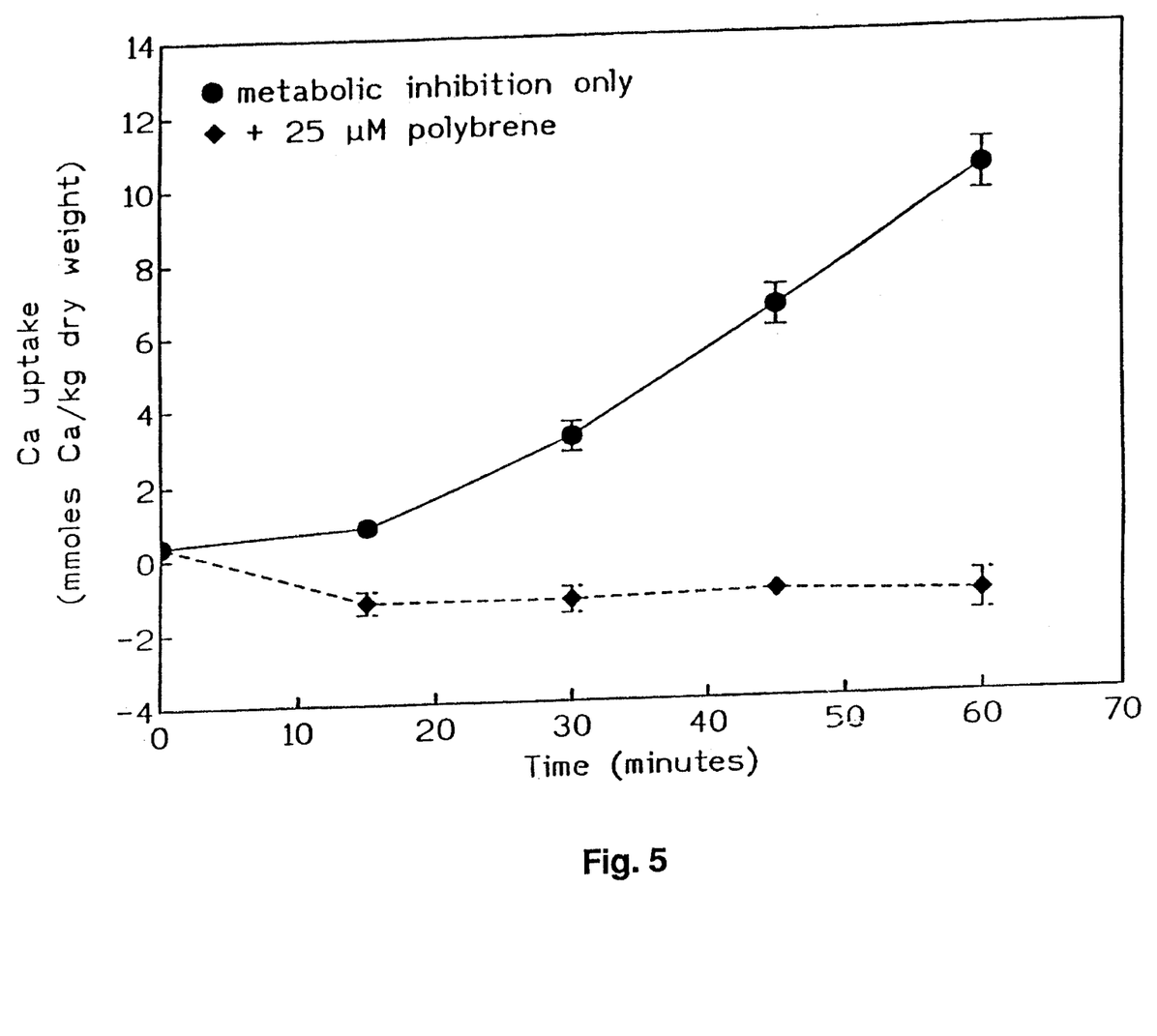
FIG. 5 is a graph of test results showing the prevention of calcium uptake by treatment of cells with polybrene where the cells have been metabolically inhibited and the polybrene concentration is 25 µM.

The same procedures were followed as in Examples 1 and 2, except that polybrene was substituted for protamine. Polybrene also inhibited the calcium leak caused by either hydrogen peroxide or metabolic inhibition. The threshold concentration above which inhibition was significant was 25 μM. The results of the tests for the polybrene/hydrogen peroxide combination are summarized and displayed in FIG. 4. The result for the polybrene/metabolic inhibition combination are shown in FIG. 5.

EXAMPLE 4

In this example, dodecyltrimethylammonium bromide(D-DTMA) was used as the cationic agent. The DDTMA was tested in the same manner as the preceding examples wherein neonatal rat cardiomyocytes were subjected to metabolic inhibition using iodoacetic acid and 2-deoxyglucose. The concentration of DDTMA was 50 μM. The DDTMA provided a significant inhibition of calcium uptake(14).

EXAMPLE 5

In this example, polymyxin B sulfate (PXB) was used as the cationic agent. The PXB was tested in the same manner as Example 4. The concentration of PXB was 100 μM. In all cases, calcium uptake was substantially inhibited(14).

EXAMPLE 6

The cationic agents of the present invention are particularly useful in those clinical situations where the heart has been deprived of its blood supply (ischemia) for variable periods of time and then resupply (reperfusion) is instituted. Such conditions are typical of acute coronary occlusion treated by dissolution of the occluding clot by various enzymes, coronary occlusion treated by coronary angioplasty or reperfusion after interruption of coronary blood flow during cardiac surgical procedures. All such situations have a high risk of producing cellular calcium overload during the reperfusion period. The overload frequently produces cell death and, if sufficient numbers of cells are involved, death of the patient.

In the above situations, the cationic agents are added directly to the reperfusion solution at a concentration found to be effective in preventing calcium overload under in vitro conditions, i.e. 5 μM for the most effective cations. At these concentrations the negative inotropic effect will be minimal and, when present, will be rapidly reversed when the cationic agent is discontinued.

Prevention of calcium overload in accordance with the present invention will increase the chance of cardiac cell survival in response to reperfusion. Such survival is important since heart muscle is incapable of regeneration and non-reversible cell damage leads to heart failure and/or death.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

BIBLIOGRAPHY

1. Farber J L: Calcium dependence of toxic cell death: A final common pathway. Science 1979;206:700–702.

2. Bourdillon, P D V; Poole-Wilson, P A, (1981) Effects of ischaemia and reperfusion on calcium exchange and mechanical function and mechanical function in isolated rabbit myocardium. Cardiovasc Res; 15: 121–130.

3. Nayler, W G; Grau, A; Slade (1976) A protective effect of verapamil on hypoxic heart muscle. Cardiovasc Res; 10:650–622.

4. Allen, D G; Orchard, C H (1983) Intracellular calcium concentration during hypoxia and metabolic inhibition in mammalian ventricular muscle. J. Physiol (London); 339: 107–122. 4.

5. Chien, K R; Engler, R (1990) Superoxide dismutase enhances recovery following myocardial ischemia. Am J Physiol; 248: H637–H643.

6. Farber, J L (1979) Calcium dependence of toxic cell death: a final common pathway. Science; 206: 700– 702.

7. Tani, M (1990) Mechanisms of $Ca^{2+}$ overload in reperfused ischemic myocardium. Annu Rev Physiol; 52:543–559.

8. Knopf, H; Theising, R; Moon, C H; Hirche, H J (1990) Continuous determination of extracellular space and changes of $K^+$, $Na^+$, $Ca^{2+}$, $H^+$ during global ischaemia in isolated rat hearts. J. Mol Cell Cardiol; 22:1259–1272.

9. Ziegelstein, R C; Sweier, J L; Mellits, E D, Younes, A; Lakatta, E G; Stern, M D; Silverman, H S (1992) Dimethylthiourea, an oxygen radical scavenger protects isolated cardiac myocytes from hypoxic injury by inhibition of Na-Ca exchange and not by its antioxidant effects. Circ Res; 70:804–811.

10. Coulombe A; Lefevre I A; Baro I; Coraboeuf E: Barium- and calcium permeable channels open at negative membrane potentials in rat ventricular myocytes. J Membr Biol 1989; 111:57–67.

11. Benham C D, Tsien R W: A novel receptor-operated $Ca^{2+}$ -permeable channel activated by ATP in smooth muscle. Nature 1987; 328: 275–278.

12. Fong P, Turner P R, Denetclaw W F, Steinhardt R A: Increased activity of calcium leak channels in myotubes of Duchenne human and mdx mouse origin. Science 1990: 250: 673–676.

13. Frank, J S; Langer, G A; Nudd, L M and Seraydarian, K. The myocardial cell surface, its histochemistry and the effects of sialic acid and calcium removal on its structure and cellular ionic exchange. Circ. Res. 41: 702–714, 1977.

14. Clague J. R. et al.: Cationic Amphiphiles Prevent

Calcium Leak Induced by ATP Depletion in Myocardial Cells. Circulation Research, Vol 72, No. 1, January 1993.

What is claimed is:

1. A method for reducing the uptake of calcium by a mammalian cell wherein said cell includes a surface having a surface charge, said method comprising the step of treating said cell surface with a sufficient amount of a cationic agent to alter the surface charge of said cell to reduce the uptake of calcium by said cell wherein said cationic agent is selected from the group consisting of protamine, dodecyltrimethylammonium bromide, polymyxin B sulfate and polybrene.

2. A method for reducing the uptake of calcium by a cell according to claim 1 wherein said cell is a muscle cell.

3. A method for reducing the uptake of calcium by a cell according to claim 2 wherein said cell surface comprises a sarcolemma.

4. A method for reducing the uptake of calcium by a cell according to claim 3 wherein said cell is a cardiac myocyte.

5. A method for reducing the uptake of calcium by a cell according to claim 1 wherein said cell is located in vivo in a mammal and wherein said cationic agent is delivered to said mammal intravenously.

6. A method for reducing the uptake of calcium by a cell according to claim 5 wherein said cell is a muscle cell.

7. A method for reducing the uptake of calcium by a cell according to claim 6 wherein said cell surface comprises a sarcolemma.

8. A method for reducing the uptake of calcium by a cell according to claim 7 wherein said cell is a cardiac myocyte.

9. In a mammalian cell having a surface through which abnormally high amounts of calcium are being taken up by said cell, wherein the improvement comprises treating the surface of said cell with a sufficient amount of a cationic agent to alter the surface charge of said cell to thereby reduce the amount of calcium which is being taken up by said cell, wherein said cationic agent is selected from the group consisting of protamine, dodecyltrimethylamonium bromide, polymyxin B sulfate and polybrene.

10. A cell treatment according to claim 9 wherein said cell is a muscle cell.

11. A cell treatment according to claim 9 wherein said cell is a cardiac myocyte.

12. A cell treatment according to claim 9 wherein said cell is located in vivo in a mammal wherein said cationic agent is delivered to said mammal intravenously.

13. A method for reducing the entry of calcium into a cell wherein said cell includes calcium leak channels through which calcium may enter said cell, said method comprising the step of treating said cell with a sufficient amount of cationic agent to alter the surface charge of said cell sufficiently to reduce the amount of calcium which is entering said cell through said calcium leak channels, wherein said cationic agent is selected from the group consisting of protamine, dodecyltrimethylammonium bromide, polymyxin B sulfate and polybrene.

14. A method for reducing the entry of calcium into a cell according to claim 13 wherein said cell is a muscle cell.

15. A method for reducing the entry of calcium into a cell according to claim 14 wherein said cell surface comprises a sarcolemma.

16. A method for reducing the entry of calcium into a cell according to claim 15 wherein said cell is a cardiac myocyte.

17. A method for reducing the entry of calcium into a cell according to claim 13 wherein said cell is located in vivo in a mammal wherein said cationic agent is delivered to said mammal intravenously.

* * * * *

UNITED STATES PATENT AND TRADEMARK OFFICE
CERTIFICATE OF CORRECTION

PATENT NO. : 5,459,126
DATED : October 17, 1995
INVENTOR(S) : Langer et al.

It is certified that error appears in the above-indentified patent and that said Letters Patent is hereby corrected as shown below:

On the title page, item:
 [73] Assignee:   should be:

--The Regents of the University of California,
   Oakland, Calif.--

Signed and Sealed this

Twenty-fifth Day of February, 1997

Attest:

BRUCE LEHMAN

*Attesting Officer*    *Commissioner of Patents and Trademarks*